United States Patent

Coty et al.

Patent Number: 5,212,081
Date of Patent: May 18, 1993

[54] STABILIZATION OF POLYPEPTIDE FRAGMENTS AGAINST PROTEOLYTIC DEGRADATION

[75] Inventors: Bill Coty, Danville; Pyare Khanna, Fremont, both of Calif.

[73] Assignee: Microgenics Corporation, Concord, Calif.

[21] Appl. No.: 503,836

[22] Filed: Apr. 3, 1990

[51] Int. Cl.$^5$ .............................................. C12N 9/96
[52] U.S. Cl. .................................... 435/188; 435/207; 530/363
[58] Field of Search .................... 435/188, 7.9, 7.7, 18, 435/14, 195, 207; 436/18, 176; 530/363

[56] References Cited

U.S. PATENT DOCUMENTS

| | | | |
|---|---|---|---|
| 2,930,736 | 3/1960 | Sullivan et al. | 435/188 |
| 4,058,596 | 11/1977 | Nachtigal | 424/50 |
| 4,378,428 | 3/1983 | Farina et al. | 435/7.4 |
| 4,409,334 | 10/1983 | Lill et al. | 436/15 |
| 4,708,929 | 11/1987 | Henderson | 435/7.8 |

FOREIGN PATENT DOCUMENTS

0040799A3  2/1981  European Pat. Off. .
0286367A3 12/1988  European Pat. Off. .
0306167A3  8/1989  European Pat. Off. .
1488988   10/1977  United Kingdom .

OTHER PUBLICATIONS

Manual of Clinical Laboratory Immunology Rose et al. (1986) pp. 99–109.
Sigma Chemical Company. (1986) pp. 141–145.
Gonnelli, et al., *Biochem + Biophys. Res. Comm.* (1981) 102:917–923.
Feder et al., *Microbiology Abstracts*, 14:7, Jul. 1979, London GB, p. 41, "Stabilization of proteolytic enzymes in solution".

*Primary Examiner*—Johnnie R. Brown
*Assistant Examiner*—Pamela S. Webber
*Attorney, Agent, or Firm*—Cooley Godward Castro Huddleson & Tatum

[57] ABSTRACT

Enzyme-donor fragments and other unstructured peptides are stabilized against proteolytic degradation by including a mixture of soluble, random-sequence peptides in the assay medium or in the medium in which the enzyme-donor fragment or other peptide is stored.

4 Claims, 2 Drawing Sheets

STABILIZATION OF POLYPEPTIDE FRAGMENTS AGAINST PROTEOLYTIC DEGRADATION

BACKGROUND AND FIELD OF INVENTION

This invention relates to techniques and compositions useful for stabilizing proteinaceous reagents and is specifically directed to stabilization of the peptide fragments derived from enzymes that are used in complementation assays.

DESCRIPTION OF THE BACKGROUND

A number of immunoassays and other binding assays have recently been described that utilize the reassociation of polypeptide fragments to form active enzymes as a step of generating a detectable signal utilized to determine the amount of analyte present in an assay mixture. Several of these assays propose using the enzyme $\beta$-galactosidase as the enzyme being formed by complementation.

However, the stability of reagents based on fragments of $\beta$-galactosidase have been discovered to be less than desirable. For example, there is a gradual but continuous and significant loss of the ability of fragments to reform into an active enzyme as storage time of the fragments increases. Stabilization of the individual $\beta$-galactosidase fragments (referred to as the enzyme-donor or ED fragment, the smaller of the two fragments, and the enzyme-acceptor or EA fragment, the larger of the two fragments) prior to combination or contact with a sample is described in U.S. patent application Ser. No. 034,757, now U.S. Pat. No. 4,956,274, filed Apr. 6, 1987 (equivalent to European Application No. 84107889.2, published Jan. 23, 1985 under Publication No. 0 131 864 A2). Sufficient stability is achieved by the method described therein, which utilizes initial storage of the enzyme fragments in the presence of a detergent followed by addition of a cyclodextrin to prevent the detergent from interfering with the complementation process, to allow long-term storage of the individual fragments.

However, storage stability of the individual fragments represents a different issue from degradation of the fragments when the fragments are contacted with a sample. Previous studies have shown that the enzyme donor (ED) is highly susceptible to proteolytic cleavage. For example, ED cannot be recovered from bacteria which express this protein unless enzyme acceptor (EA) is present so that active $\beta$-galactosidase is formed. Additionally, patient samples contaminated with bacteria exhibit low values in enzyme complementation assays, which result from degradation of ED-analyte conjugate during the assay These patient samples can be shown to contain bacterial protease activity by a variety of assays. The effects of protease contamination can be, reduced, but not eliminated, by inclusion of protease inhibitors, such as aprotinin or PMSF, in the assay medium or preferably in the ED reagent.

Loss of enzyme activity due to ED destruction in bacteria-contaminated serum therefore presents an undesirable problem for the analyst. If an assay reading is low, a separate assay of proteolytic activity is desirable to eliminate the possibility of bacterial contamination. Such an additional assay is cumbersome and slows down the speed with which accurate assay results can be obtained. An effective technique for protecting enzyme-donor fragments against proteolytic degradation is therefore desirable.

RELEVANT PUBLICATIONS

An immunoassay system based on the reassociation of polypeptide fragments is described by Farina and Golkey, U.S. Pat. No. 4,378,428, issued Mar. 20, 1983, and by Gonelli, et al., *Biochem. and Biophys. Res. Commun.* (1981) 102:917–923. The molecular nature of $\beta$-galactosidase $\alpha$-complementation is described in a Ph.D. thesis of this title by Langley, UCLA, 1975. An assay system based on natural and modified $\beta$-galactosidase polypeptides in a complementation assay is described in U.S. Pat. No. 4,708,929 and PCT Application No. PCT/US Ser. No. 85/02095, having an international publication date of May 9, 1986.

SUMMARY OF THE INVENTION

The present invention provides techniques for stabilizing enzyme-donor fragments from $\beta$-galactosidase and other active-peptides of simple structure against proteolytic degradation. Proteolytic degradation is avoided by including in the medium in which proteolysis is likely to occur, typically a sample assay medium containing serum, a mixture of linear peptide fragments substantially without secondary structure. Since the specificity of the protease activity is generally not known, a random mixture of linear peptides is used. Random fragment mixtures have shown almost complete inhibition of ED degradation for up to twenty minutes of incubation of serum with enzyme-donor fragments.

BRIEF DESCRIPTION OF THE DRAWINGS

The present invention will be better understood by reference to the following detailed description of the invention when considered in combination with the drawings that form part of the specification, wherein.

DESCRIPTION OF SPECIFIC EMBODIMENTS

Figure 1:
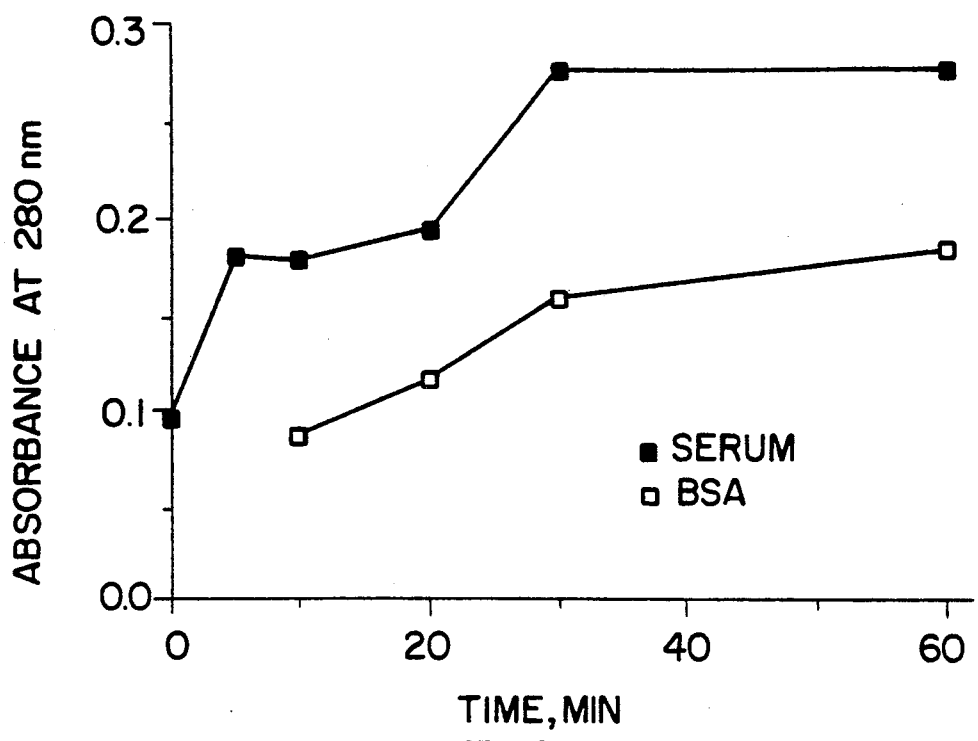
FIG. 1 is a graph showing time dependence of protein hydolysis used to prepare random mixtures of linear peptides used as protecting peptides in the present invention.

The enzyme-donor (ED) fragment being protected by the process and compositions of the present invention is a relatively short (typically from 60 to 100 amino acids) linear peptide substantially without secondary structure; i.e., it contains little or no $\alpha$-helix, $\beta$-sheet, or other structural features prior to association with the enzyme-acceptor (EA) fragment and formation of the active enzyme. Peptides without secondary structure are particularly susceptible to proteolytic cleavage, as there is little or no structure to interfere with the amino acid chain assuming the necessary confirmation for cleavage. Furthermore, when ED is contacted with serum that is contaminated with bacteria of unknown origin, there is no way of predicting the specificity of the proteolytic activity that will be present in a sample.

Accordingly, specific inhibitors, although they may prove useful in some cases, are not generally useful in an analytical setting.

The present inventors have discovered that proteolytic degradation of ED can be essentially halted by including in the reaction mixture a random mixture of soluble, linear peptide fragments of random sequence. These fragments will not interfere with the complementation assay, since the complementation is quite specific. They will, however, compete with ED for the binding sites on proteolytic enzymes, thereby decreasing the degradation of ED.

The invention as described herein has been developed and is particularly useful for protecting against degradation of enzyme-donor fragments used in α-complementation assays, specifically when the enzyme from which the fragments are derived is β-galactosidase or a modified β-galactosidase molecule. The invention is also generally applicable to protecting specific linear peptides substantially without secondary structure of other origin against proteolytic degradation. Examples of other protein fragments and small unstructured peptides that can be protected include bioactive peptides such as ACTH, endorphins, and oxytoxcin. The remainder of this discussion exemplifies the general technique using the β-galactosidase ED fragment, but the technique can be applied to the protection of other fragments by substituting the other desirable fragments for the ED fragment.

"Without" secondary structure, as used herein, means no secondary structural features (i.e., the peptide is in a linear, extended conformation in solution). "Substantially without" means that at least a degradable portion of the total sequence of the peptide has no secondary structure, preferably at least 25% of the amino acids in the total sequence (those amino acids without secondary structure preferably being at one of the two termini), more preferably at least 50%, even more preferably at least 75%. It is recognized that in solution some temporary association of amino acids into secondary structures is likely to occur, and that such associations do not modify the designation of the class of active peptides molecules that can be protected by the present invention.

The protective peptides of the present invention have a number of general and specific characteristics but are characterized in one manner, by its very nature, difficult to describe precisely: both the length and the sequences of the peptides that form the protective composition are deliberately selected to vary widely. Although it is possible to use automated peptide synthesis techniques to prepare a mixture containing precisely defined varying sequences and lengths, such a process would be unduly expensive and is generally not preferred. When synthetic techniques are used, true random generation of peptide mixtures is preferred, such as by reacting unprotected mixtures of amino acids. Linear peptides without secondary structure can also easily be obtained by proteolytic cleavage of larger peptides that do have secondary (and tertiary) structure, such as human serum proteins, bovine serum albumin (BSA), mmunoglobulins, and egg white proteins. These proteins can be cleaved randomly using a variety of proteolytic enzymes, such as pepsin, trypsim, chymotrypsin, papin, chymopapain, and subtilisin. Pepsin and other enzymes that are active under acidic conditions are particularly preferred to facilitate protein breakdown, since the acidic conditions promote denaturation.

As is well understood by those skilled in the art of protein chemistry, preparation of peptide fragments by enzymatic degradation is not truly random in the statistical sense, since the enzymes used for proteolysis will have particular specificities for each type of the possible dipeptide pairs that form a cleavable amide bond. Thus, a protein such as bovine serum albumin treated with an enzyme such as pepsin will be preferentially cleaved at certain locations. However, since proteolysis of large proteins to form the protective peptide mixtures will be limited rather than complete, there is considerable variation in the cleavage sites and length of peptides that will exist in any given mixture. Furthermore, random hydrolytic cleavage can occur under acidic conditions, and different preparations of the starting protein may contain different contaminating proteins, so that the result can truly be referred to as random, even though some regularity can occur in the cleavage process. Accordingly, the word "random" is used throughout to describe both the sequence and the length of the protective peptides.

When the protective peptide composition of the invention is prepared by hydrolysis of a large organized protein, hydrolysis is limited rather than complete so that the resulting peptide mixture contains a variety of peptides of different length rather than being hydrolyzed all the way to individual amino acids. The mixture usually contains peptides ranging in length from 2 to about 200 amino acids, preferably from 30 to 90 amino acids, and most preferably about 60 to 80 amino acids. These lengths are also preferred for random synthetic mixtures.

Since different proteolytic enzymes will have different rates of cleavage and since different proteins will be cleaved at different rates, conditions such as time, temperature, and concentration of reagents will be varied according to the particular protein and enzyme being used. Exemplary procedures are set forth in the examples that follow. However, those skilled in the art of protein chemistry will understand that significant variations can be made while achieving essentially the same result. For example, temperatures can be raised to increase the reaction rate while lowering the concentration of proteolytic enzyme will decrease the reaction rate. A useful and easily carried out test for the production of protective peptides is measuring the appearance of soluble peptides in a solution containing from 5–10%, preferably about 6.25% of trichloroacetic acid (TCA). Such TCA solutions will typically precipitate large proteins, so that the appearance of soluble peptides in a TCA solution is indication of cleavage of the parent proteins by the proteolytic enzymes. These soluble peptides can be determined by any peptide analysis system, such as absorbance at 280 nm.

Since protection is believed to occur by competition between protective peptides and the desirable bioactive peptide, any amount of the protective peptide mixture will reduce proteolytic cleavage of the desirable bioactive peptide to some extent. It is preferred to use at least a 10-fold excess (by weight) of protective to bioactive peptide. Higher ratios (e.g., $10^2:1$, $10^4:1$, $10^6:1$, $10^8:1$, $10^{10}:1$, or higher) can be used, limited only by the solubility of the protective peptides and the required concentration of the bioactive peptide. Weight ratios can be prepared either by actual weighing or by analytical processes used to determine relative amounts of proteins and peptides, such as light absorbance at 280 nm or colorimetric assays (either of which can be carried out on known dilutions of the protective peptide mixture to obtain more accurate results).

When a proteolytic enzyme is used to prepare protective peptide mixtures, it is necessary to inactivate the proteolytic enzyme or separate it from the mixture before the resulting protective mixture is contacted with an ED-containing medium. For example, enzymes such as pepsin can be inactivated by immersing the pepsin-containing composition in a boiling water bath for 20 minutes. Other enzymes can be inactivated using specific conditions known to inactivate those enzymes. Since the protective peptides do not have secondary structure, techniques used to deactivate proteolytic enzymes by destroying their secondary and tertiary structures will not adversely effect the protective peptides that are present in the same composition. Size fractionation (e.g., gel filtration) can also be used to separate the large active molecules from the desired small peptide fragments.

The enzyme-donor fragments protected by the present invention are fully described in the patent applications, patents, and other publications cited above. A full description of the ED component is therefore not required at this time. However, a brief description is provided here for the sake of those who are less familiar with this assay technology. Complementation assays are those in which two enzyme fragments, neither of which is active by itself, recombine in a step known as a complementation step to form an active enzyme. Thus, complementation assays belong generally to the class of assays in which an enzyme acts as a reporter and quantitated based on the amount of enzyme activity present in the assay medium, usually measured by the production of a substrate by the enzyme. Accordingly, the enzyme acts to amplify the presence of the analyte.

A number of variations on complementation assays exists. In one typical assay, an analog of the analyte for example, digoxin) is attached to the enzyme-donor fragment. The analog by itself is not of a sufficient size to interfere with the complementation process. Accordingly, if only the labelled ED fragment and enzyme acceptor (EA) fragment are present, an active enzyme will result from a complementation step. However, if an antibody binds to the analyte analog that is attached to the ED fragment, complementation cannot take place because of the bulk of the antibody. In an assay medium containing only ED/analyte conjugate, antibody to the analyte, and EA, no complementation will take place. In the presence of analyte, however, some of the antibody will bind to the analyte, thereby freeing ED-/analyte conjugate to react with EA and provide active enzyme. Higher concentrations of analyte in the sample will cause the production of more active enzyme as the analyte binds more of the antibody. Accordingly, the amount of analyte can be quantitated by the amounts of enzyme that has reformed.

When the reporter enzyme is $\beta$-galactosidase, the ED fragment is typically a segment from the amino-terminase of the complete peptide. Such fragments are typically about 90 amino acids in length and have used the same amino acid sequence as that of natural $\beta$-galactosidase or a sequence that has been slightly varied from the natural sequence to increase stability, provide for easier attachment of analyte, or for other purposes well known to those who use this assay analytically. For a number of variations, see the patents and other publications cited above.

Since the purpose of the present invention is to protect ED against proteolytic degradation arising from proteolytic assay in the sample, there are a number of techniques that can be used when combining the various components of an assay medium containing ED and protective peptides. For example, the protective peptide mixture can be added to the sample either prior to or concurrently with adding the ED fragment to the sample. It is also possible to include the protective peptide mixture in the ED storage composition, so that manipulation is minimized. Furthermore, since the rate of degradation of complemented enzyme activity is reduced by proteolytic degradation (when present) by only about one percent per minute, it is also possible to add the protective peptide mixture to the assay composition after ED has been contacted with the medium. However, prior addition of the protective peptide is preferred, particularly inclusion of the protective peptide mixture in the ED storage medium.

It is preferred to include the protective peptide mixture in the ED storage composition, since it appears that some protection against storage degradation is provided by the protective peptide mixture. In some cases sufficient storage stability is provided so that detergents and cyclodextrins, as described in U.S. patent application Ser. No. 034,757, cited above, are not required. The degree of protection varies with the specific assay and may depend on the analyte or analyte analog attached to the ED fragment. However, since including the protective peptide mixture in the storage medium also reduces the number of manipulative steps that must be carried out when the assy is being conducted and since the protective peptide mixture has no adverse effect on the assay, inclusion of the mixture in the storage medium is desirable even if no protection against storage degradation would be provided.

No additional manipulative steps are required for use of a protective peptide composition of the invention in a complementation assay. A general assay is described below. Specific details, including exact times, temperature, and other reaction conditions are set forth in the examples that follow.

In a typical assay of a human serum sample, a reaction mixture is prepared containing an appropriate aliquot of the human serum, a diluent solution containing a buffer to optimize the complementation assay conditions, a protective peptide mixture to prevent proteolytic degradation of the ED fragment, and preselected amounts of ED/analyte conjugate and EA. Substrate for complemented enzyme can be present in the initial reaction mixture or can be added later. In most cases, conversion of substrate in the product will e measured photometrically at a wave length at which the product absorbs but the substrate does not. A photometric measurement is then made either of the rate of conversion of substrate product or of the amount of product formed at a particular time. By comparing the result of this photometric measurement to the results of analyses run on sample containing known amounts of analyte, the amount of analyte in the sample can be determined.

It should be recognized that practice of the present invention requires manipulation by the user and that the invention is not intended to cover situations in which mixtures of peptides are naturally present as a result of proteolytic cleavage that has begun but which is not yet complete. The invention does involve deliberate protection of a biologically active peptide by including in a composition (either by adding directly to the composition or to a precursor of the composition) a protective mixture of peptides as described herein.

The invention now being generally described, the same will be better understood by reference to the following detailed examples which are provided for purposes of illustration only and are not to be limiting of the invention unless so specified.

EXAMPLE 1

Preparation of Protective Peptides by Hydrolysis of Serum Proteins

Five mL of serum (human serum from Biocell) was diluted with 5 mL of deionized water and then divided into 1 mL aliquots. To each aliquot was added 400 μL of 0.1 M HCl (resulting in a pH of 3.3) and 50 μL of pepsin (Porcine Pepsin form Sigma; 1 mg/mL in 1 mM HCl). The mixtures were incubuated at 37° C. for various time intervals: 0. 5, 10, 20, 30 and 60 min. After incubation, the reaction mixtures were treated with 100 μL 0.5 M $K_2HPO_4$ and incubated in a boiling water bath for 20 minutes to inactivate the pepsin. The mixtures were cooled and centrifuged for 15 minutes, and supernatant fractions containing the neutralized serum protein hydrolysates were removed for testing.

EXAMPLE 2

Preparation of Protective Peptide Mixtures by Hydrolysis of BSA

Bovine Serum Albumin (BSA; Sigma 0.3 g) was dissolved in 6 mL of deionized water, and then divided into 1 mL aliquots. To each aliquot was added 350 μL of 0.1 M HCl (resulting in a pH of 3.1) and 50 μL of pepsin (1 mg/mL in 1 mM HCl). The mixtures were incubated at 37° C. for varying intervals: 10, 20, 30 and 60 min. The reaction mixtures were treated with 100 μL 0.6 M $K_2HPO_4$ and incubated in a boiling water bath for 20 minutes to inactivate the pepsin. The mixtures were cooled and centrifuged for 15 minutes. The supernatant fractions containing the neutralized BSA hydrolysates were removed for testing as described below.

EXAMPLE 3

Measurement of Protein Hydrolysis

The extent of protein hydrolysis in each of the different incubations described above in Examples 1 and 2 was evaluated by measuring the release of TCA-soluble peptides by their absorbance at 280 nm. Fifty μL of each hydrolysate was diluted with 700 μL of deionized water and 250 μL of 25% (w/v) Trichloroacetic Acid (TCA). The mixtures were chilled on ice for 15 minutes. The mixtures were then centrifuged for 15 minutes, and the supernatant fractions decanted into separate tubes. The absorbance of the separate fractions was measured at 280 nm, using a solution containing 750 μL water and 250 μL 25% TCA as a blank. The results of these hydrolyses are shown in FIG. 1.

EXAMPLE 4

Effect of Protein Hydrolysates on ED Stability

The effect of protein hydrolysates on ED stability was measured by pre-incubating a serum sample with ED in the presence and absence of the various protein hydrolysates, followed by a two-step automated measurement of ED activity.

The initial incubation contained 80 μL of human serum (the test serum being analyzed), 20 μL of a diluent solution (80 mM sodium phosphate, 10 mM EGTA, 20 mM sodium azide, 0.1% BSA, pH 6.9), 80 μL of either the protein hydolysate being tested for protective activity or assay buffer (60mM potassium phosphate, 0.4 M NaCl, 10 mM EGTA, 3 mM magnesium acetate, 20 mM sodium azide, 0.05% Tween-20, pH 7.0) in a Hitachi sample cup. Twenty μL of a 0.23 nM solution of ED-digoxin in assay buffer was added last, and this mixture was incubated for varying times at room temperature (about 22° C). The different incubations were started so that the ending times were at 40-second intervals (twice the sampling time of the automated Hitachi 704 analyzer to allow duplicate determinations).

The mixtures were placed on the sample rotor of the Hitachi 704 analyzer, and the assay was started at the end of the pre-incubation period. The assay steps began by adding 20 μL of sample mixture and 200 μL of EA Reagent (containing 100 units of EA in assay buffer) to the cuvette, mixing, and incubating for 5 minutes at 37° C. One hundred thirty μL of Substrate Reagent containing 2.6 mg Chlorophenolred-μ-D-galactopyranoside (CPRG; Boehringer Mannheim Biochemicals) per mL in assay buffer (as described above) was added, mixed, and incubated at 37° C. The rate of change of absorbance per minute at 570 nm was measured between about 70 and about 130 seconds after addition of substrate.

Figure 2:
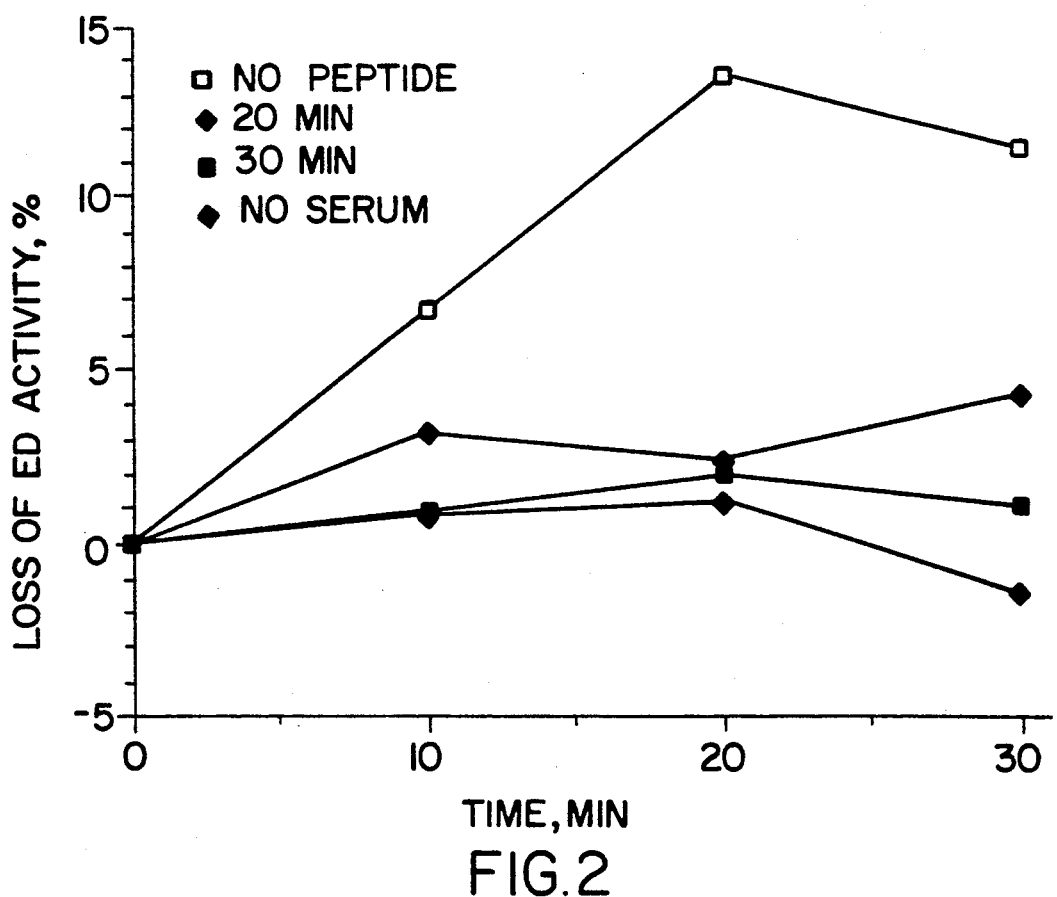
FIG. 2 is a graph showing the loss of ED activity upon incubation with serum and reduction of this loss when the same sample is incubated in the presence of random linear peptides.
Figure 3:
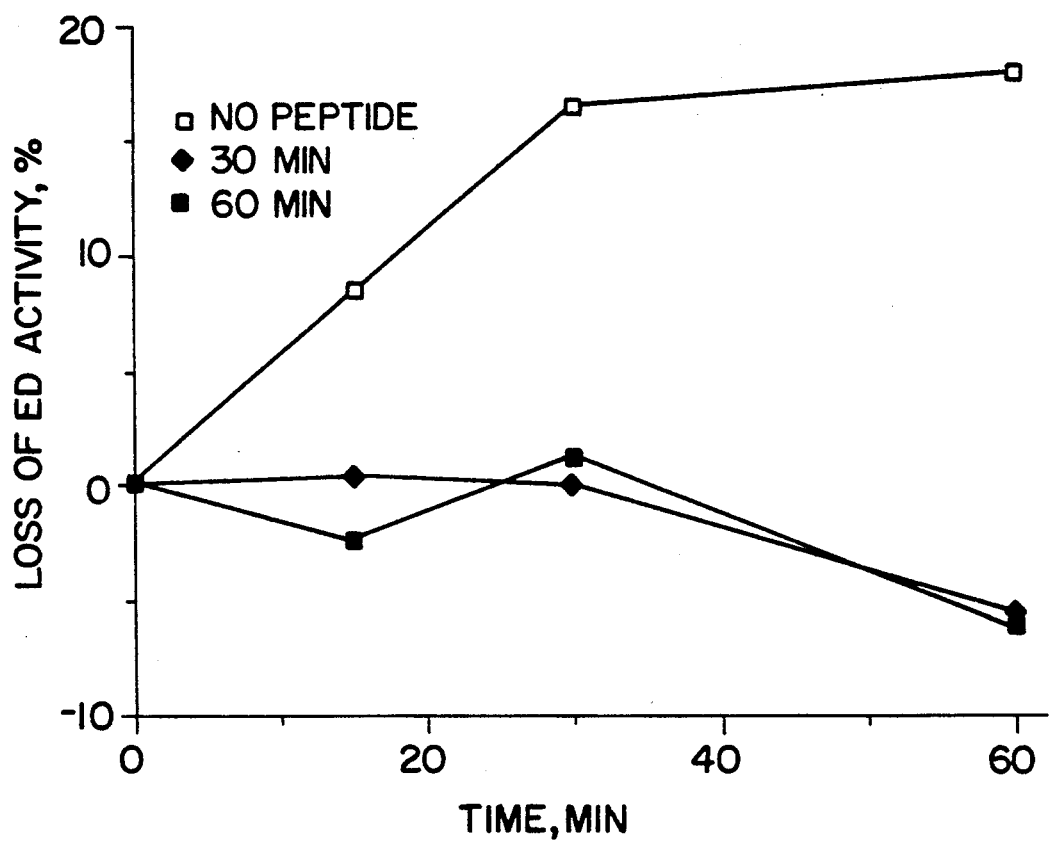
FIG. 3 is a graph showing the loss of ED activity upon incubation with serum and reduction of this loss of activity when a sample is incubated in the presence of a different mixture of randum linear peptides than that shown in FIG. 2.

The results of these assays are graphed in FIG. 2 (Serum Protein Hydrolysates) and FIG. 3 (BSA Hydrolysates).

ED degradation was rapid during the first 10 minutes upon incubation with test serum in the absence of protecting proteins, and this degradation slowed or plateaued at some point between 10 and 30 minutes, as shown by the example of the specific assay described above and shown in FIG. 2 (the "No Peptide" line). The loss of ED activity was caused by the presence of human serum in the incubation; in the absence of serum no degradation occurred (see the "No Serum" line of FIG. 2). The protective peptides obtained by pepsin hydrolysis of serum showed almost complete inhibition of ED degradation for up to 30 minutes after incubation of serum and ED began, using both the 20- and 30-minute hydrolysates. Somewhat greater inhibition was obtained using the 30-minute hydrolysate compared to the 20-minute hydrolysate.

The protective peptides obtained by pepsin hydrolysis of BSA also inhibited ED degradation as shown in FIG. 3. Inhibition was more complete than with the serum hydrolysates, and inhibition lasted for up to 60 minutes of incubation of serum with ED. Little difference was seen between the 30-minute hydrolysate and the 60-minutes hydrolysate.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of stabilizing a beta-galactosidase enzyme-donor fragment in a complementation assay which comprises:

including in an assay medium in which said assay is carried out a mixture of soluble, random-sequence peptides, wherein said mixture comprises a hydrolysate of bovine serum albumin or human serum proteins, in an amount sufficient to reduce proteolytic degradation of said enzyme-donor fragment.

2. A composition for stabilizing an enzyme-donor fragment form beta-galactosidase against proteolytic degradation in a complementation assay, which comprises a solution containing said enzyme-donor fragment and a mixture of soluble, random-sequence peptides, herein said mixture comprises a hydrolysate of bovine serum albumin or human serum proteins, in an amount sufficient to stabilize said fragment against proteolysis when said composition is added to a serum sample.

3. The composition of claim 2, wherein said peptides and said fragment are present at a weight ratio of at least 10:1.

4. A method of stabilizing a biologically active, linear peptide substantially without secondary structure against proteolytic degradation, which comprises:
including in a medium which contains said active peptide and in which said proteolytic cleavage occurs a mixture of soluble, random-sequence peptides, wherein said mixture comprises a hydrolysate of bovine serum albumin or human serum proteins, in an amount sufficient to reduce proteolysis of said active peptide.

* * * * *